(12) United States Patent
Castro (10) Patent No.: US 6,783,547 B2
(45) Date of Patent: Aug. 31, 2004

(54) APPARATUS FOR FUSING ADJACENT BONE STRUCTURES

(75) Inventor: Michael Castro, Seymour, CT (US)

(73) Assignee: Howmedica Corp., Allendale, NJ (US)

( * ) Notice: Subject to any disclaimer, the term of this patent is extended or adjusted under 35 U.S.C. 154(b) by 60 days.

(21) Appl. No.: 10/118,205

(22) Filed: Apr. 5, 2002

(65) Prior Publication Data

US 2003/0191535 A1 Oct. 9, 2003

(51) Int. Cl.[7] ............................................... A61F 2/44
(52) U.S. Cl. ................................................... 623/17.16
(58) Field of Search .......................... 623/17.11, 17.13, 623/17.15, 17.16

(56) References Cited

U.S. PATENT DOCUMENTS

| | | | | |
|---|---|---|---|---|
| 4,401,112 A | * | 8/1983 | Rezaian | 606/61 |
| 4,553,273 A | * | 11/1985 | Wu | 623/23.45 |
| 4,599,086 A | | 7/1986 | Doty | |
| 4,636,217 A | | 1/1987 | Ogilvie et al. | |
| 4,657,550 A | * | 4/1987 | Daher | 623/17.11 |
| 4,743,256 A | | 5/1988 | Brantigan | |
| 4,834,757 A | | 5/1989 | Brantigan | |
| 4,878,915 A | | 11/1989 | Brantigan | |
| 4,880,343 A | * | 11/1989 | Matsumoto | 411/222 |
| 4,932,975 A | * | 6/1990 | Main et al. | 623/17.12 |
| 5,192,327 A | | 3/1993 | Brantigan | |
| 5,236,460 A | | 8/1993 | Barber | |
| 5,246,458 A | | 9/1993 | Graham | |
| 5,290,312 A | | 3/1994 | Kojimoto et al. | |
| 5,306,310 A | | 4/1994 | Siebels | |
| 5,336,223 A | | 8/1994 | Rogers | |
| 5,390,683 A | * | 2/1995 | Pisharodi | 128/898 |
| 5,405,391 A | * | 4/1995 | Hednerson et al. | 623/17.15 |
| 5,413,602 A | * | 5/1995 | Metz-Stavenhagen | 623/17.15 |

(List continued on next page.)

FOREIGN PATENT DOCUMENTS

| | | | | | |
|---|---|---|---|---|---|
| DE | 3023942 | * | 1/1982 | | 623/17.11 |
| DE | 4012622 | * | 7/1991 | | 623/17.11 |
| DE | 19509317 | * | 9/1996 | | 623/17.11 |
| EP | 0567424 | * | 10/1993 | | 623/17.11 |
| EP | 1 080 703 | | 3/2001 | | |
| FR | 2636227 | * | 9/1988 | | 623/17.11 |
| WO | WO9525486 | * | 9/1995 | | 623/17.11 |
| WO | WO97000054 | * | 1/1997 | | 623/17.11 |
| WO | WO-99/38462 | | 8/1999 | | |
| WO | WO-00/78253 A1 | | 12/2000 | | |

OTHER PUBLICATIONS

European Search Report dated Nov. 3, 2003.

*Primary Examiner*—Eduardo C. Robert
(74) *Attorney, Agent, or Firm*—Lerner, David, Littenberg, Krumholz & Mentlik, LLP (57) ABSTRACT

An apparatus for facilitating fusion of adjacent vertebral portions includes an implant member dimensioned for positioning between adjacent vertebral portions and defining a longitudinal axis. The implant member includes an outer member having an exterior wall defining an internal cavity and a clip receiving opening subtending a peripheral portion of the exterior wall, an inner member telescopically received within the internal cavity of the outer member to permit relative movement of the outer and inner members and a locking clip dimensioned for at least partial reception within the clip receiving opening of the outer member. The inner member includes an exterior wall defining an internal cavity and having a plurality of locking slots spaced along the longitudinal axis. The locking clip includes a clip base and locking clip legs depending from opposed ends of the clip base. The locking clip legs are dimensioned for reception within corresponding locking slots of the inner member to selectively secure a relative position of the outer and inner members to establish a predetermined height of the implant member.

16 Claims, 6 Drawing Sheets

U.S. PATENT DOCUMENTS

| | | | |
|---|---|---|---|
| 5,443,515 A | | 8/1995 | Cohen et al. |
| 5,458,641 A | | 10/1995 | Ramirez Jimenez |
| 5,522,899 A | | 6/1996 | Michelson |
| 5,571,190 A | | 11/1996 | Ulrich et al. |
| 5,571,192 A | | 11/1996 | Schönhöffer |
| 5,575,790 A | * | 11/1996 | Chen et al. .................. 606/60 |
| 5,591,235 A | * | 1/1997 | Kuslich ..................... 606/61 |
| 5,609,637 A | | 3/1997 | Biedermann et al. |
| 5,653,763 A | * | 8/1997 | Errico et al. ............. 623/17.11 |
| 5,665,122 A | | 9/1997 | Kambin |
| 5,683,394 A | | 11/1997 | Rinner |
| 5,683,463 A | * | 11/1997 | Godefroy et al. ........ 623/17.16 |
| 5,693,100 A | * | 12/1997 | Pisharodi ................ 623/17.16 |
| 5,702,449 A | | 12/1997 | McKay |
| 5,702,451 A | | 12/1997 | Biedermann et al. |
| 5,702,453 A | | 12/1997 | Rabbe et al. |
| 5,702,455 A | | 12/1997 | Saggar |
| 5,713,904 A | | 2/1998 | Errico et al. |
| 5,720,746 A | | 2/1998 | Soubeiran |
| 5,723,013 A | * | 3/1998 | Jeanson et al. ......... 623/17.16 |
| 5,725,580 A | | 3/1998 | Cloutier et al. |
| 5,776,197 A | | 7/1998 | Rabbe et al. |
| 5,776,198 A | | 7/1998 | Rabbe et al. |
| 5,776,199 A | | 7/1998 | Michelson |
| 5,827,328 A | | 10/1998 | Buttermann |
| 5,865,848 A | | 2/1999 | Baker |
| 5,897,556 A | | 4/1999 | Drewry et al. |
| 5,916,267 A | | 6/1999 | Tienboon |
| 5,972,031 A | | 10/1999 | Biedermann et al. |
| 5,980,522 A | | 11/1999 | Koros et al. |
| 5,989,290 A | * | 11/1999 | Biedermann et al. .... 623/17.11 |
| 6,015,436 A | * | 1/2000 | Schonhoffer ............. 623/17.16 |
| 6,037,519 A | | 3/2000 | McKay |
| 6,039,762 A | | 3/2000 | McKay |
| 6,086,613 A | | 7/2000 | Camino et al. |
| 6,123,705 A | | 9/2000 | Michelson |
| 6,126,660 A | | 10/2000 | Dietz |
| 6,149,651 A | | 11/2000 | Drewry et al. |
| 6,159,211 A | | 12/2000 | Boriani et al. |
| 6,159,244 A | | 12/2000 | Suddaby |
| 6,174,334 B1 | | 1/2001 | Suddaby |
| 6,176,881 B1 | * | 1/2001 | Schar et al. ............. 623/17.11 |
| 6,176,882 B1 | | 1/2001 | Biedermann et al. |
| 6,190,413 B1 | | 2/2001 | Sutcliffe |
| 6,193,755 B1 | | 2/2001 | Metz-Stavenhagen et al. |
| 6,193,756 B1 | | 2/2001 | Studer et al. |
| 6,200,348 B1 | | 3/2001 | Biedermann et al. |
| 6,217,579 B1 | | 4/2001 | Koros |
| 6,296,665 B1 | * | 10/2001 | Strnad et al. ............ 623/17.16 |
| 6,344,057 B1 | * | 2/2002 | Rabbe et al. ............ 623/17.11 |
| 6,419,705 B1 | * | 7/2002 | Erickson .................. 623/17.16 |
| 6,524,341 B2 | * | 2/2003 | Läng et al. ............... 623/17.15 |
| 2003/0074063 A1 | * | 4/2003 | Gerbec et al. ........... 623/16.11 |

* cited by examiner

APPARATUS FOR FUSING ADJACENT BONE STRUCTURES

BACKGROUND

1. Technical Field

The present disclosure generally relates to a surgical apparatus for fusing adjacent bone structures, and, more particularly, to an apparatus and associated method for fusing adjacent vertebrae.

2. Background of the Related Art

The fusion of adjacent bone structures is commonly performed to provide for long-term replacement to compensate for degenerative or deteriorated disorders in bone. For example, an intervertebral disc, which is a ligamentous cushion disposed between adjacent vertebrae, may undergo deterioration as a result of injury, disease, tumor or other disorders. The disk shrinks or flattens leading to mechanical instability and painful disc translocations.

Figure 1:
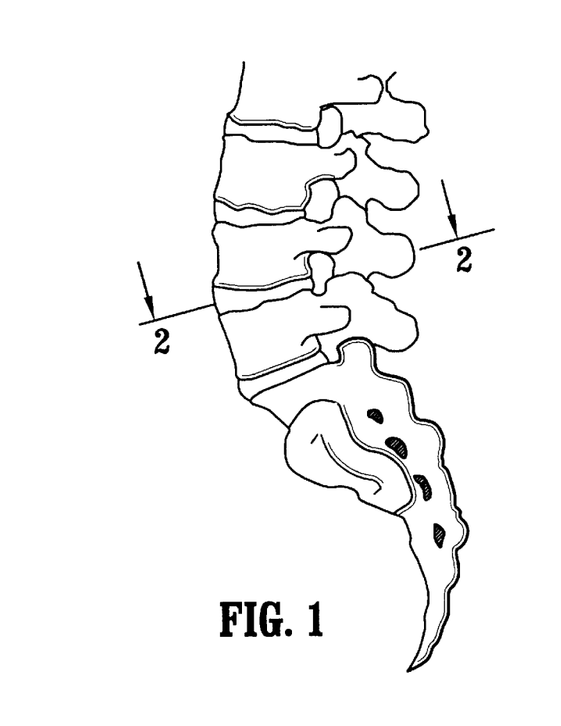
FIG. 1 is a view illustrating a portion of the vertebral column of a patient.
Figure 2:
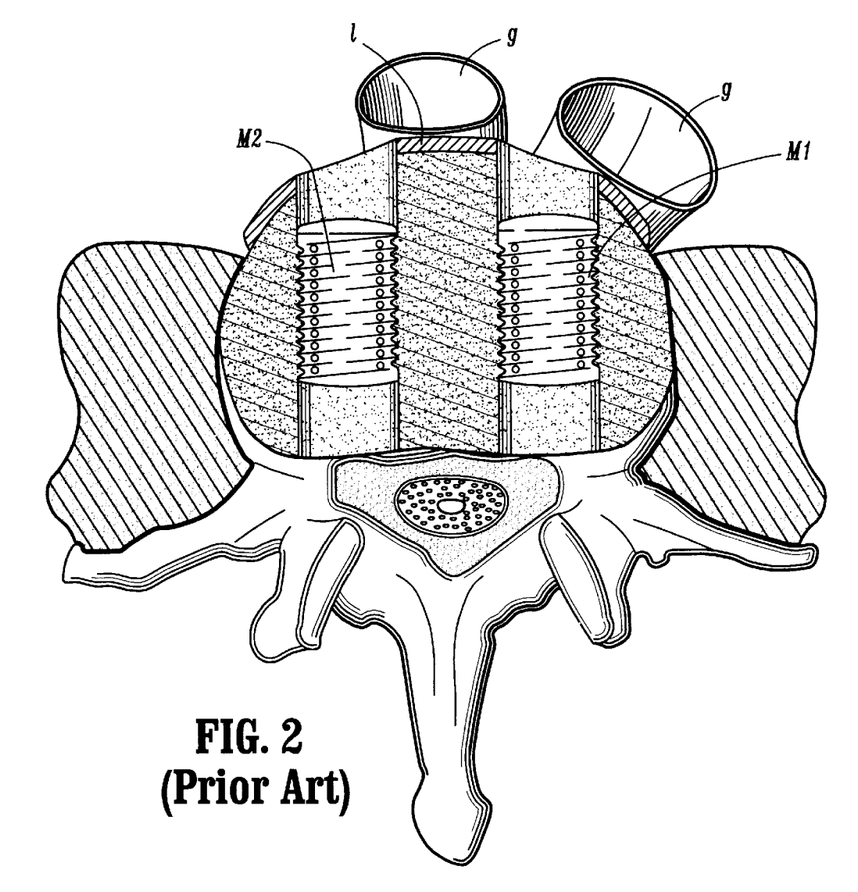
FIG. 2 is a view taken along lines 2—2 of FIG. 1 illustrating a pair of prior art fusion implants positioned within the intervertebral space for fusion of adjacent vertebrae.

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. More recently, emphasis has been placed on fusing bone structures (i.e., adjoining vertebrae) with metallic or ceramic prosthetic cage implants. One fusion cage implant is disclosed in commonly assigned U.S. Pat. No. 5,026,373 to Ray et al., the contents of which are incorporated herein by reference. The Ray '373 fusion cage includes a cylindrical cage body having a thread formed as part of its external surface and apertures extending through its wall which communicate with an internal cavity of the cage body. The fusion cage is inserted within a tapped bore or channel formed in the intervertebral space thereby stabilizing the vertebrae and maintaining a predefined intervertebral space. Preferably, a pair of fusion cages are implanted within the intervertebral space. The adjacent vertebral bone structures communicate through the apertures and with bone growth inducing substances which are within the internal cavity to unite and eventually form a solid fusion of the adjacent vertebrae. FIGS. 1–2 illustrate the insertion of a pair of the Ray '373 fusion cages positioned within an intervertebral space.

SUMMARY

Accordingly, the present invention is directed to further improvements in spinal fusion procedures. In accordance with a preferred embodiment, an apparatus for facilitating fusion of adjacent bony structures includes an outer implant member with an implant wall having outer and inner wall surfaces and defining an internal cavity and an inner implant member at least partially disposed within the internal cavity of the outer implant member and adapted for movement relative thereto. The inner implant member includes an implant wall having outer and inner wall surfaces and defining at least one locking slot portion therein. The apparatus further includes a locking clip which is mountable to the outer wall surface of one of the outer and inner implant members. The locking clip includes a locking arm arranged for reception within the one locking slot of the inner member and being dimensioned to engage the outer wall of the outer member to secure a relative position of the inner and outer members. The locking clip may further include a clip base and opposed locking arms depending from the base. The opposed locking arms are dimensioned for reception within corresponding locking slot portions of the inner implant member. The outer and inner implant members are preferably dimensioned for positioning between adjacent vertebral bodies.

In an alternative embodiment, the apparatus for facilitating fusion of adjacent vertebral portions includes an implant member dimensioned for positioning between adjacent vertebral portions and defining a longitudinal axis. The implant member includes an outer member having an exterior wall defining an internal cavity and a clip receiving opening subtending a peripheral portion of the exterior wall, an inner member telescopically received within the internal cavity of the outer member to permit relative movement of the outer and inner members and a locking clip dimensioned for at least partial reception within the clip receiving opening of the outer member. The inner member includes an exterior wall defining an internal cavity and has a plurality of locking slots spaced along the longitudinal axis. The locking clip includes a clip base and locking clip legs depending from opposed ends of the clip base. The locking clip legs include clip projections which are dimensioned for reception within corresponding locking slots of the inner member to selectively secure a relative position of the outer and inner members to establish a predetermined height of the implant member. The clip base of the locking clip may include a clip projection dimensioned for reception within a corresponding locking slot of the inner member. The inner member preferably includes a series of locking slots defined in the exterior wall thereof and spaced along the longitudinal axis. Each series includes a pair of spaced slot portions for reception of the locking clip legs and an intermediate slot portion for reception of the clip base.

The exterior wall of the outer member may include a plurality of perforations extending in communication with the internal cavity thereof to permit bone growth therethrough. Similarly, the exterior wall of the inner member may also include a plurality of perforations extending in communication with the internal cavity thereof to permit bone growth therethrough. An end cap may be releasably mounted to a longitudinal end of one of the inner and outer members. Bone growth inducing substances may be disposed within the internal cavities of the inner and outer members to facilitate bone ingrowth.

A method for supporting vertebral portions is also disclosed. The method includes the steps of accessing adjacent vertebral portions, providing an implant apparatus including an outer member having an exterior wall defining an internal cavity and an inner member telescopically received within the internal cavity of the outer member and having an exterior wall defining an internal cavity and a plurality of locking slots spaced along the longitudinal axis, extending the outer and inner members of the implant member to a predetermined length, positioning a locking clip within the clip receiving opening of the outer member whereby locking clip legs of the locking clip are received within corresponding locking slots of the inner member to selectively secure a relative position of the outer and inner members to establish a predetermined height of the implant member and introducing the implant apparatus within a space defined between two vertebral portions. An end cap may be mounted to exposed ends of the inner and outer members. Bone graft material may be introduced within the internal cavities to facilitate bone ingrowth.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

The preferred embodiment of the apparatus and method disclosed herein are discussed in terms of orthopedic spinal fusion procedures and instrumentation. It is envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of the fusion implant utilized in performing a spinal fusion followed by a description of the preferred method for spinal fusion in accordance with the present disclosure.

In the discussion which follows, the term "proximal", as is traditional, will refer to the portion of the structure which is closer to the operator while the term "distal" will refer to the portion which is further from the operator.

Figure 4:
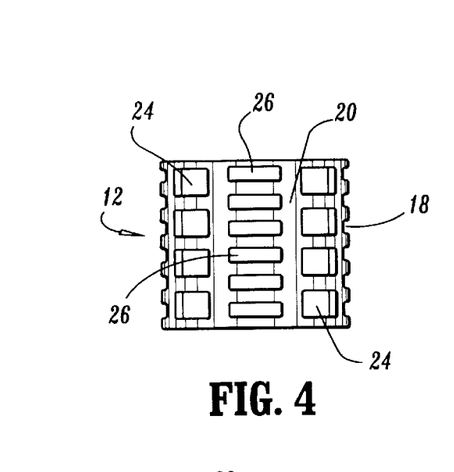
FIGS. 4–5 are side plan views of the inner cage of the implant apparatus.
Figure 5:
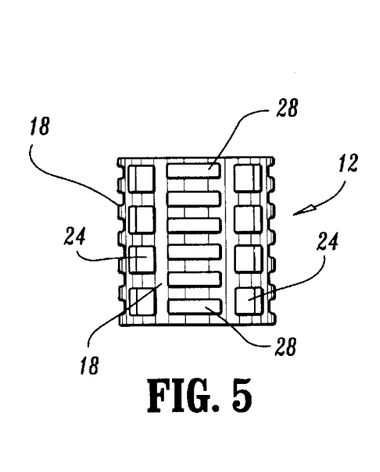
Figure 6:
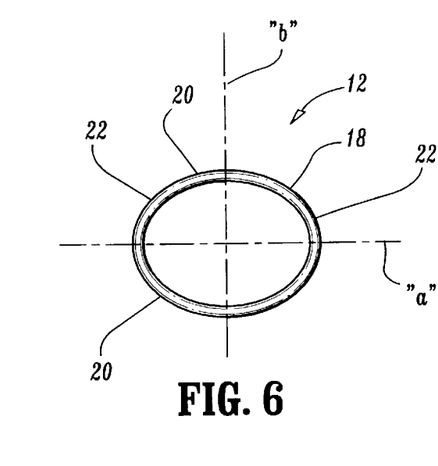
FIG. 6 is a top plan view of the inner cage.

The apparatus is particularly intended for use in maintaining the normal spacing between vertebral bodies subsequent to a discectomy procedure or subsequent to the removal of a vertebral body portion from the spinal column to facilitate interbody fusion of the vertebrae. With initial reference to FIG. 3, apparatus 10 includes inner cage 12, outer cage 14 which telescopically receives the inner cage 12 and C-clip 16 which secures the relative position of the inner and outer cages 12, 14. As illustrated in FIGS. 4–6, in conjunction with FIG. 3, inner cage 12 includes exterior cage wall 18 having a general oval cross-sectional dimension defining opposed major and minor arc wall sections 20, 22 with respect to major and minor axes "a, b". Exterior wall 18 has a plurality of relatively large rectangular shaped openings 24 extending through the major and minor arc wall arc sections 18, 20 in communication with the interior of the inner cage 12 to permit bone ingrowth to facilitate the fusion process. Exterior wall 18 further includes first locking slots 26 in each major arc section 20 and disposed in spaced relation along the longitudinal axis "x" of the implant 10. Second locking slots 28 are defined within each minor arc section 22 of the exterior wall 18 and disposed in spaced relation along the axis "x" of the implant 10. Locking slots 26, 28 disposed at the same location with respect to the axis "x" of the implant form a series of locking slots to enable the operator to securely and selectively lock, with C-clip 16, the relative positioning of the inner and outer cages 12, 14 as will be discussed.

Figure 3:
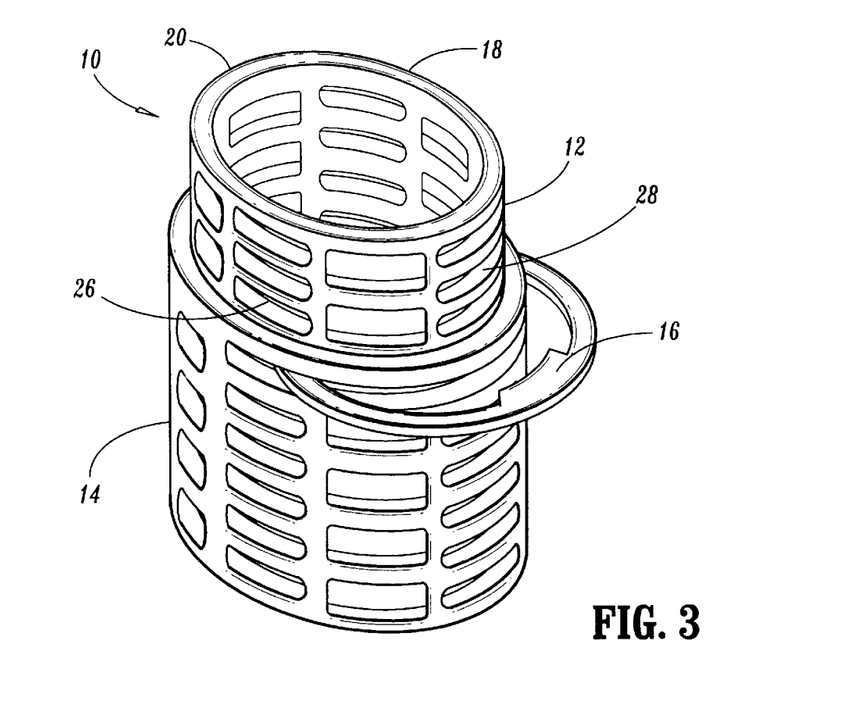
FIG. 3 is a perspective view of the fusion implant apparatus in accordance with the principles of the present disclosure illustrating the inner cage, outer cage and C-clip.
Figure 7:
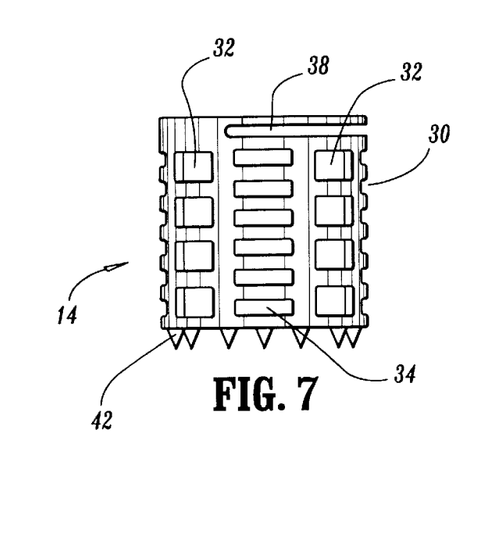
FIGS. 7–8 are side plan views of the outer cage of the implant apparatus.
Figure 8:
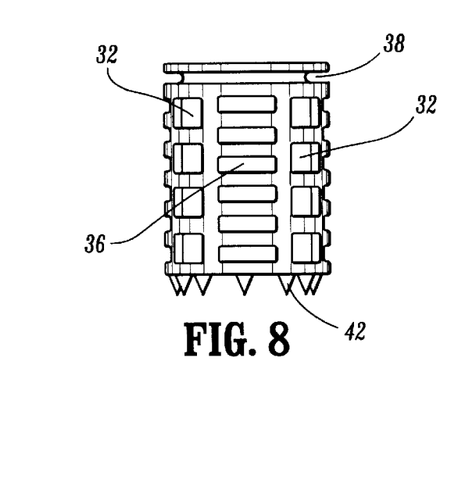
Figure 9:
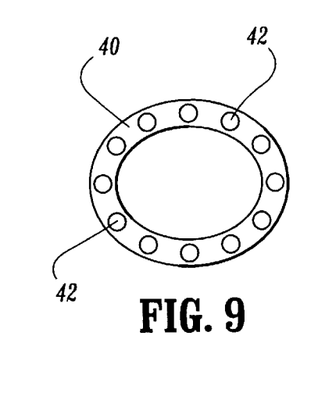
FIG. 9 is a top plan view of the outer cage illustrating the bone engaging projections for engaging the vertebral bone.

Referring now to FIGS. 7–9 in view of FIG. 3, outer cage 14 is similar in construction to inner cage 12. Outer cage 14 includes cage wall 30 having a general oval cross-sectional dimension and large rectangular openings 32 extending through the wall 30. A plurality of slots 34, 36 also extend through cage wall 30 in respective major and minor arc sections of the wall 30. In the preferred embodiment, openings 32 and slots 34, 36 are intended to permit bone ingrowth within outer cage 14 to facilitate the fusion process. Cage wall 30 of outer cage 14 further includes clip receiving opening 38 disposed adjacent the upper end of the outer cage 14. Clip receiving opening 38 subtends an arc greater than approximately 180 deg of cage wall 30. Clip receiving opening 38 is dimensioned to accommodate C-clip 16.

Outer cage 14 may include an integrally formed end face 40 at one longitudinal end, which contacts the vertebral body when appropriately positioned within the intervertebral space. End face 40 may include a plurality of conical shaped projections 42 extending from the end face 40. Projections 42 are preferably sharpened to penetrate the vertebral tissue to facilitate retention within the vertebral bodies. Alternatively, outer cage 14 may be devoid of end face 40.

Figure 10:
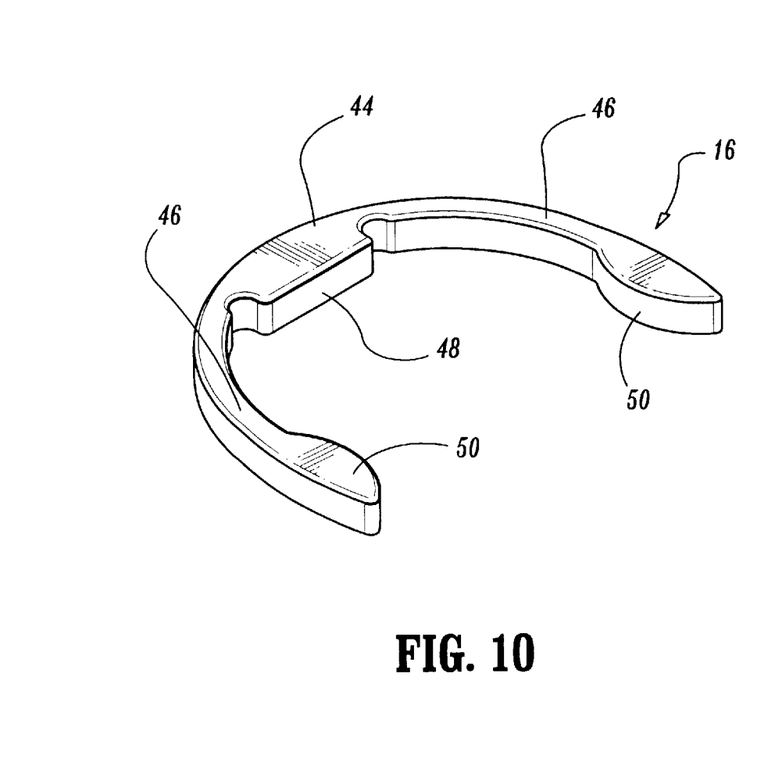
FIG. 10 is a perspective view of the C-clip of the implant apparatus.
Figure 11:
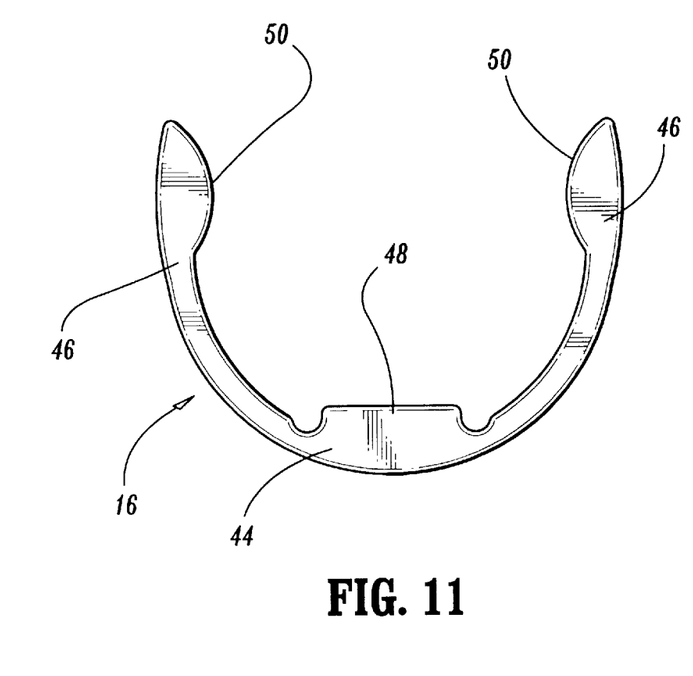
FIG. 11 is a side plan view of the C-clip.
Figure 12:
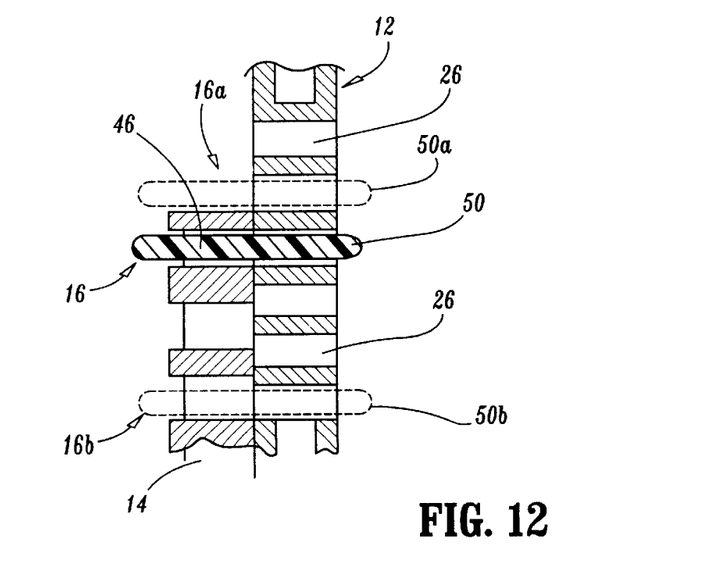
FIG. 12 is a cross-sectional view illustrating engagement of the locking clip projection of the C-clip with the inner and outer cages.

With reference now to FIGS. 10–11, in view of FIG. 3, C-clip 16 will be discussed in detail. C-clip 16 includes clip base 44 and clip legs 46 depending from opposed ends of the clip base 44. Clip base 44 includes locking projection 48. Similarly, clip legs 44 include locking projections 50. Locking projection 48 is received within one of the locking slots 26 of minor arc section 22 of inner cage 12 when C-clip 16 is in a secured position. Locking projections 50 are received within corresponding axially located locking slots 26 of major arc section 20 of inner cage 12 when in the secured position of C-clip 16. FIG. 12 illustrates in cross-section the locking relationship of locking projection 50 of one of the clip legs 46 within a corresponding locking slot 38 of outer cage 14. As shown, locking projection 50 extends for a sufficient distance through locking slot 38 to engage inner cage 12 and extend within the locking slot 26 of the inner cage 12. This secures the relative positioning of the inner and outer cages 12, 14. C-clip 16 is preferably resilient to permit outward deflection of clip legs 46 upon positioning of the C-clip 16 relative to inner and outer cages 12, 14 while returning to its normal unstressed condition to secure the C-clip to the implant 10. Suitable materials of construction for C-clip 16 includes resilient metals such as stainless steel, titanium or alloys thereof, in addition to resilient polymeric materials.

Alternatively, C-clip 16a may be positioned adjacent the upper end of inner cage 12 as shown in phantom in FIG. 12 to extend within a corresponding series of locking slots 26, 28 of inner cage 12. (In FIG. 12, locking projection 50a is shown in phantom in the secured position). With this arrangement, the relative position of inner and outer cages 12 is secured in a compressive direction of the implant 10. In a further alternative, locking projection 50b of C-clip 16b (shown in phantom in FIG. 12) may be positioned within a series of locking slots 34, 36 of outer cage 14 to extend within an aligned or corresponding series of locking slots 26, 28 of inner cage 12. With this arrangement, locking projection 50b has a greater degree of extension or length to be received within the slots of the inner and outer cages 12, 14.

Inner and outer cage 12, 14 are each preferably fabricated from a suitable biocompatible rigid material such as titanium and/or alloys of titanium, stainless steel, ceramic materials or rigid polymeric materials. Apparatus 10 is preferably sufficient in strength to at least partially replace the supporting function of an intervertebral disc, i.e., to maintain adjacent vertebrae in desired spaced relation, during healing and fusion. Various heights and dimensions of apparatus 10 are contemplated depending on the surgical approach. Inner and outer cages 12, 14 may also be circular in cross-section.

Figures 13, 14, 15:
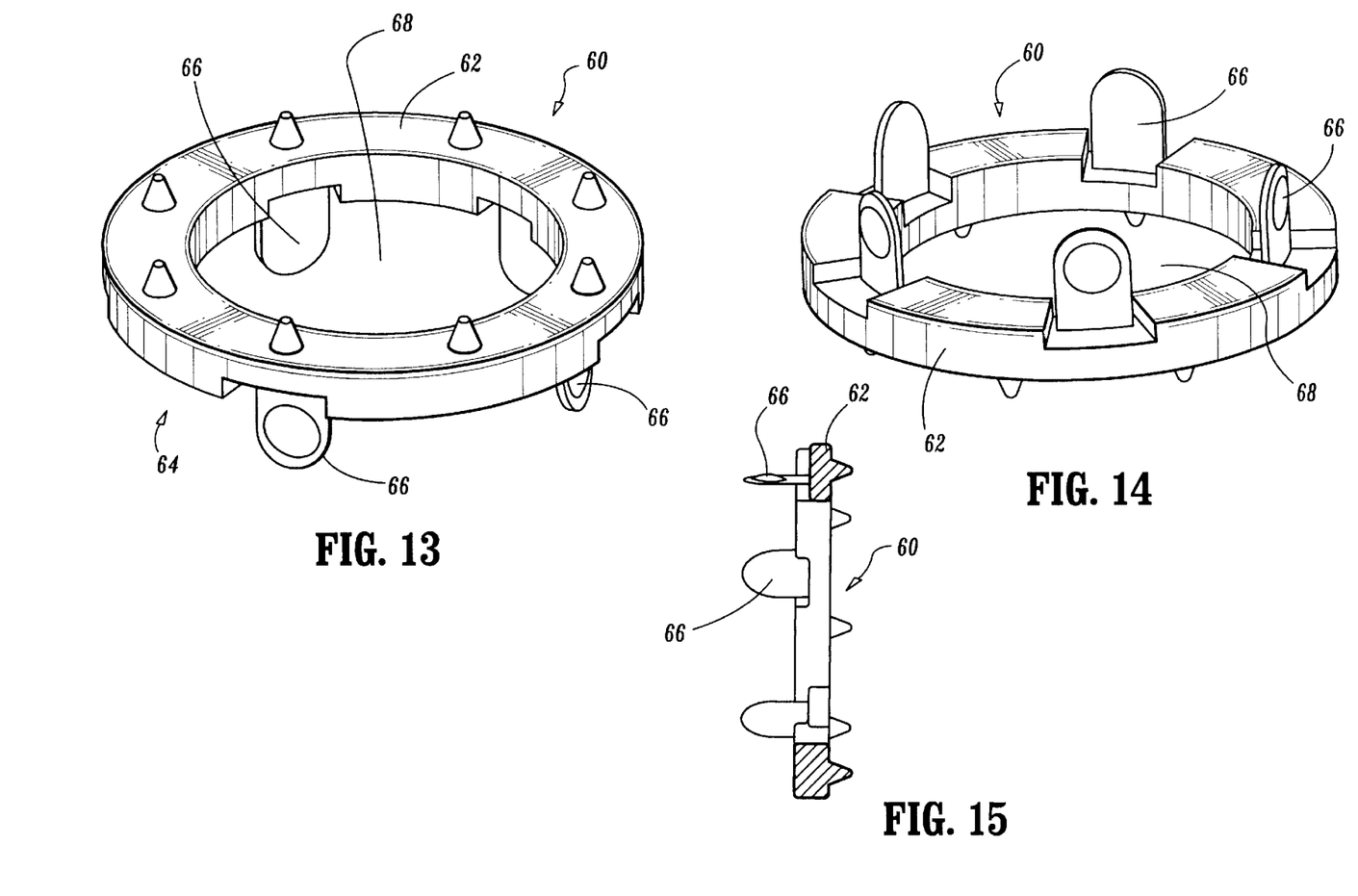
FIGS. 13–14 are perspective views of an end cap for use with the implant apparatus.
FIG. 15 is a cross-sectional view of the end cap of FIGS. 13–14.

With reference to FIGS. 13–15, apparatus 10 may further include end caps 60 which are mounted to one or both of the exposed longitudinal ends (depending whether outer cage or inner cage is provided with an end face) of the inner and outer cages 12, 14. Each end cap 60 includes peripheral collar 62 and insertion portion 64 depending from the collar 62. Collar 62 defines an enlarged cross-section relative to the longitudinal ends of inner and outer cages 12, 14 to engage the respective ends of the cages 12, 14. Insertion portion 64 includes a plurality of arcuate internal springs 66 depending axially from the collar 62. Internal springs 66 are adapted to flex inwardly upon positioning of end cap 60 within the respective cage, but, return outwardly under the influence of their resilient characteristics, to engage the inner surfaces of the inner or outer cages 12, 14, thereby securing the end cap 60 to the respective cage 12, 14. Arcuate springs 66 may be connected to collar 62 by conventional means and are preferably fabricated from a resilient plastic or metallic material. End cap 60 further defines central opening 68. End cap 60 is shown circular in cross-section for use with a circular inner and outer cage 12, 14 although it is appreciated that end cap 60 may be elliptical if desired. A plurality of spaced individual cone-shaped spikes 70 extend from collar 62 for penetrating the vertebral end plates when the apparatus is positioned within the intervertebral space.

Apparatus 10 is preferably implanted in conjunction with a lateral or anterior lateral surgical approach for spinal reconstruction. With reference to the flow chart of FIG. 16, initially the intervertebral space is prepared by removing all or a portion of the targeted intervertebral space and part of the adjacent vertebral end plates to form a bed for reception of the implant 10 (Step 100). Inner cage 12 is positioned within outer cage 14. Thereafter, inner cage 12 and outer cage 14 are extended to achieve a desired overall height of the apparatus (Step 200). Once the desired height is ascertained, C-clip 16 is positioned within clip receiving opening 38 of outer cage 14. It is appreciated that C-clip 16 may be at least partially inserted within clip receiving opening 38 prior to extension of outer and inner cages 12, 14. C-clip 16 is then advanced within clip receiving opening 38 whereby clip legs 46 deflect outwardly and then return inwardly to position locking projections 50 of the clip legs 46 within opposed locking slots 26 of major arc wall section 18 and locking projection 48 of clip base 44 is received within minor arc wall section 22. In this secured position of C-clip 16, the relative positioning of inner and outer cages 12, 14 is secured (Step 300).

Figure 16:
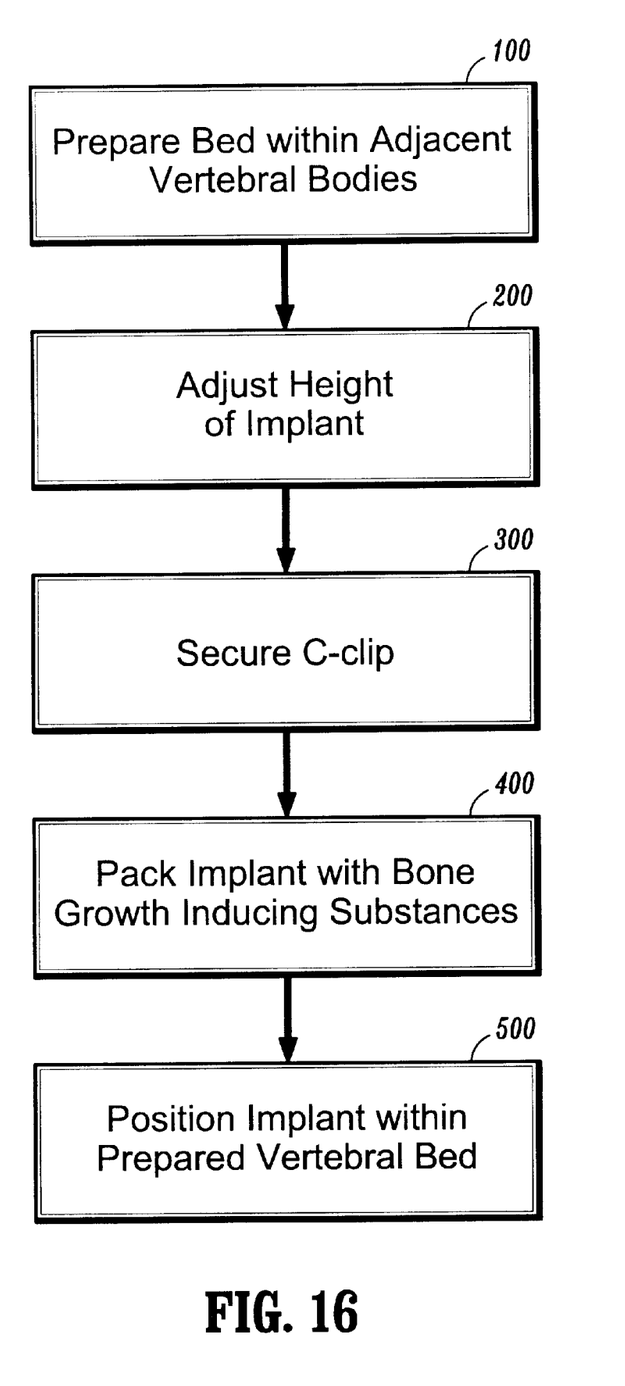
FIG. 16 is a flow chart illustrating a sequence of steps for positioning the implant apparatus within the intervertebral space of adjacent vertebral bodies.

Thereafter, the interiors of inner and outer 12, 14 are optionally filled with bone graft material, e.g., individual allograft or autograft bone chips, e.g., 5–10 mm in size, and/or other bone growth inducing substances (Step 400). End caps 60 are positioned on the exposed ends of the outer and inner cages 12, 14. The implant 10 is positioned within the bed prepared between the adjacent vertebrae (Step 500).

Implants 10 forms a strut across the intervertebral space "i" to maintain the adjacent vertebrae "$V_1$, $V_2$" in appropriate spaced relation during the fusion process. Over a period of time, the adjacent vertebral tissue communicates through apertures of outer and inner cages 12, 14 to form a solid fusion. Two implants 10 may be placed in side by side relation if desired.

While the above description contains many specifics, these specifics should not be construed as limitations on the scope of the disclosure, but merely as exemplifications of preferred embodiments thereof. For example, the fusion implant 10 could also be used for thoracic and cervical vertebrae. Those skilled in the art will envision many other possible variations that are within the scope and spirit of the disclosure as defined by the claims appended hereto.

What is claimed is:

1. An apparatus for facilitating fusion of adjacent bony structures, which comprises:

an outer implant member including an implant wall having outer and inner wall surfaces and defining an internal cavity;

an inner implant member at least partially disposed within the internal cavity of the outer implant member and adapted for movement relative thereto, the inner implant member including an implant wall having outer and inner wall surfaces and defining at least one locking slot portion therein; and a locking clip mountable to the outer wall surface of one of the outer and inner implant members, the locking clip having a locking arm arranged for reception within the one locking slot of the inner member and being dimensioned to engage the outer wall of the outer member to secure a relative position of the inner and outer members.

2. The apparatus according to claim 1 wherein the outer and inner implant members are dimensioned for positioning between adjacent vertebral bodies.

3. The apparatus according to claim 1 wherein the locking clip includes a clip base and opposed locking arms depending from the base, the opposed locking arms dimensioned for reception within corresponding locking slot portions of the inner implant member.

4. An apparatus for facilitating fusion of adjacent vertebral portions, which comprises:

an implant member dimensioned for positioning between adjacent vertebral portions and defining a longitudinal axis, the implant member including:

an outer member having an exterior wall defining an internal cavity and having a clip receiving opening subtending a peripheral portion of the exterior wall;

an inner member telescopically received within the internal cavity of the outer member to permit relative movement of the outer and inner members, the inner member including an exterior wall defining an internal cavity and having a plurality of locking slots spaced along the longitudinal axis; and a locking clip dimensioned for at least partial reception within the clip receiving opening of the outer member, the locking clip including a clip base and locking clip legs depending from opposed ends of the clip base, the locking clip legs having leg projections dimensioned for reception within corresponding locking slots of the inner member to selectively secure a relative position of the outer and inner members to establish a predetermined height of the implant member.

5. The apparatus according to claim 4 wherein the clip base includes a base projection dimensioned for reception within a corresponding locking slot of the inner member.

6. The apparatus according to claim 5 wherein the inner member includes a series of locking slots defined in the exterior wall thereof and spaced along the longitudinal axis, each series including a pair of spaced slot portions for reception of the locking clip legs and an intermediate slot portion for reception of the clip base.

7. The apparatus according to claim 4 wherein the exterior wall of the outer member includes a plurality of perforations extending in communication with the internal cavity thereof to permit bone growth therethrough.

8. The apparatus according to claim 7 wherein the exterior wall of the inner member includes a plurality of perforations extending in communication with the internal cavity thereof to permit bone growth therethrough.

9. The apparatus according to claim 4 further including an end cap releasably mounted to a longitudinal end of one of the inner and outer members.

10. The apparatus according to claim 4 including bone growth inducing substances disposed within the internal cavities of the inner and outer cage members.

11. The apparatus according to claim 4 wherein each of the inner and outer members define an oval cross-sectional dimension.

12. A method for supporting vertebral portions, comprising the steps of:

accessing adjacent vertebral portions;

providing an implant apparatus including an outer member having an exterior wall defining an internal cavity and an inner member telescopically received within the internal cavity of the outer member, the inner member including an exterior wall defining an internal cavity and having a plurality of locking slots spaced along the longitudinal axis;

extending the outer and inner members of the implant member to a predetermined length;

positioning a locking clip within the clip receiving opening of the outer member, whereby locking clip legs of the locking clip are received within corresponding locking slots of the inner member to selectively secure a relative position of the outer and inner members to establish a predetermined height of the implant member; and introducing the implant apparatus within a space defined between two vertebral portions.

13. The method according to claim 12 further including the step of mounting an end cap to an exposed end of one of the inner and outer members.

14. The method according to claim 13 further including the step of inserting bone graft material within the internal cavities of the inner and outer members.

15. An apparatus for facilitating fusion of adjacent bony structures, which comprises:

an outer implant member including an implant wall having outer and inner wall surfaces and defining an internal cavity;

an inner implant member at least partially disposed within the internal cavity of the outer implant member and adapted for movement relative thereto, the inner implant member including an implant wall having outer and inner wall surfaces and defining at least one locking slot portion therein; and a locking clip mountable to the outer wall surface of one of the outer and inner implant members, the locking clip having at least two arms, wherein at least on arm is a locking arm arranged for reception within the one locking slot of the inner member and being dimensioned to engage the outer wall of the outer member to secure a relative position of the inner and outer members.

16. The apparatus according to claim 15, wherein the outer and inner implant members are dimensioned for positioning between adjacent vertebral bodies.

* * * * *

UNITED STATES PATENT AND TRADEMARK OFFICE
CERTIFICATE OF CORRECTION

PATENT NO. : 6,783,547 B2
DATED : August 31, 2004
INVENTOR(S) : Michael Castro

It is certified that error appears in the above-identified patent and that said Letters Patent is hereby corrected as shown below:

Title page,
Item [73], Assignee, after "Howmedica" insert -- Osteonics --.

Column 6,
Line 36, after "clip" insert -- non-threadably --.
Line 38, "arranged" should read -- configured --.
Lines 39 and 40, "and being dimensioned to engage" should read -- while engaging --.

Column 7,
Line 2, "dimensioned" should read -- configured --.
Line 4, after "member" insert -- while engaging the exterior wall of the outer member --.

Column 8,
Line 6, after "member" insert -- while engaging the exterior wall of the outer member --.
Line 33, "on" should read -- one --.
Line 34, "arranged" should read -- configured --.
Lines 35 and 36, "and being dimensioned to engage" should read -- while engaging --.

Signed and Sealed this

Eighth Day of March, 2005

JON W. DUDAS
*Director of the United States Patent and Trademark Office*